United States Patent [19]

Orton, Jr.

[11] Patent Number: Plant 7,732

[45] Date of Patent: Dec. 3, 1991

[54] DOGWOOD TREE- 'RUTLAN'

[75] Inventor: Elwin R. Orton, Jr., Somerville, N.J.

[73] Assignee: Rutgers University, New Brunswick, N.J.

[21] Appl. No.: 560,547

[22] Filed: Jul. 30, 1990

[51] Int. Cl.[5] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

An $F_1$ hybrid of *Cornus kousa* Hance and *C. florida* L. providing a new large-bracted dogwood, which is an exceptionally vigorous, highly floriferous, small, flowering tree, more nearly like *C. florida*, being full and spreading in habit rather than vase-shaped as in *C. kousa*, yet considerably larger as compared with *C. florida*, and having a period of floral display that is intermediate to that of the parental species.

1 Drawing Sheet

BACKGROUND OF THE DISCLOSURE

This invention relates to a large-bracted dogwood cultivar, which is one of those developed in an extensive program of interspecific hybridization, in an effort to produce characteristics which are desirable in dogwood trees and the results have justified my efforts I believe.

The particular cultivar hereof, as one of a series of dogwood trees resulting from an extensive period of development, embodies characteristics which make the same commercially attractive and thereby having substantial potential for commercial distribution.

The interspecific hybridization in this instance is that of an unnamed seedling of *Cornus kousa* and a plant of *Cornus florida* known as 'Hillenmeyer' which is unpatented.

Some of the characteristics which I have provided as a result of my program, and which this particular cultivar exhibits, include a tall, spreading habit and a much larger tree than certain low, spreading plants of which a companion plant Cornus×'Rutfan' (U.S. Plant Pat. No. 7,206) is exemplary. Other plants developed generally during the same period of time are more erect in habit and differ in possessing floral bracts of different size, shape, texture, and/or color.

This particular cultivar, is one of a group which will be referred to in general and in some instances, specifically, by comparison for identification and other purposes.

The instant cultivar which I have chosen to designate for commercial identification as 'Rutlan', is one of a number of dogwood cultivars which I have developed, and it is compared herein with certain of the others which are also designated by their commercial names, and plant patent numbers where applicable.

It will be understood that the parental species *C. florida* and *C. kousa* have been used as a basis for the cultivars referred to and thus many of the characteristics will be found as common, yet each in turn is distinctive in its own way.

I note that plants of this species combination have not been reported previously, by anyone other than myself.

Field plantings of the instant cultivar 'Rutlan' in the vicinity of New Brunswick, N.J., do not reveal infestation by the dogwood borer nor have they exhibited "dogwood decline."

I am thus of the opinion that the plant 'Rutlan', hereof may be grown wherever plants of the parental species *C. florida* and/or *C. kousa* are grown and will exhibit the desirable characteristics and distinctions set forth herein.

In comparison with the upright habit of 'Rutban', (U.S. Plant Pat. No. 7,205) 'Rutdan', (U.S. Plant Pat. No. 7,204) and 'Rutgan', (U.S. Plant Pat. No. 7,207), plants of 'Rutlan' are spreading in habit, flower earlier, have a distinctly lower number of true flowers per flower head, and exhibit floral bracts that do not overlap; in addition, the floral bracts of 'Rutlan' provide a white floral display in the spring in contrast with the bracts of 'Rutgan' which provide a spring floral display of pink bracts. The plant form of 'Rutlan' is wider than tall in contrast with the erect (taller than wide) form of 'Rutcan', (U.S. Plant Pat. No. 7,210) in addition, the floral display of 'Rutlan' typically begins two days earlier than that of 'Rutcan'; also the white floral bracts of 'Rutlan' are shorter and wider than those of 'Rutcan'. The floral display of 'Rutlan' typically starts only one day earlier than that of 'Rutfan' (U.S. Plant Pat. No. 7,206) and the number of true flowers per flower head in these two hybrids is quite similar; however, plants of 'Rutlan' are much larger and exhibit a height/width ratio that is higher than that for plants of 'Rutfan' (approximately 0.82 versus 0.58); furthermore, the foliar bracts of 'Rutlan' are longer and wider than those of 'Rutfan'.

My new hybrid is highly sterile.

In order to summarize the various characteristics which are notable in my new cultivar, I have broken down the aspects of the same regarding tree shape, flower buds, bracts and other characteristics which will be set forth hereinafter in the specific succinct summaries noted below.

I have caused the cultivar of my new dogwood tree to be reproduced asexually by grafting, budding or rooting of stem cuttings and found that it retains its distinguishing characteristics from generation to generation.

When color is referred to, The Royal Horticultural Society Colour Chart is availed of and the colors are as nearly true as is possible to make the same in an illustration of this character, made by photographic means.

In the drawing

Figure 1:
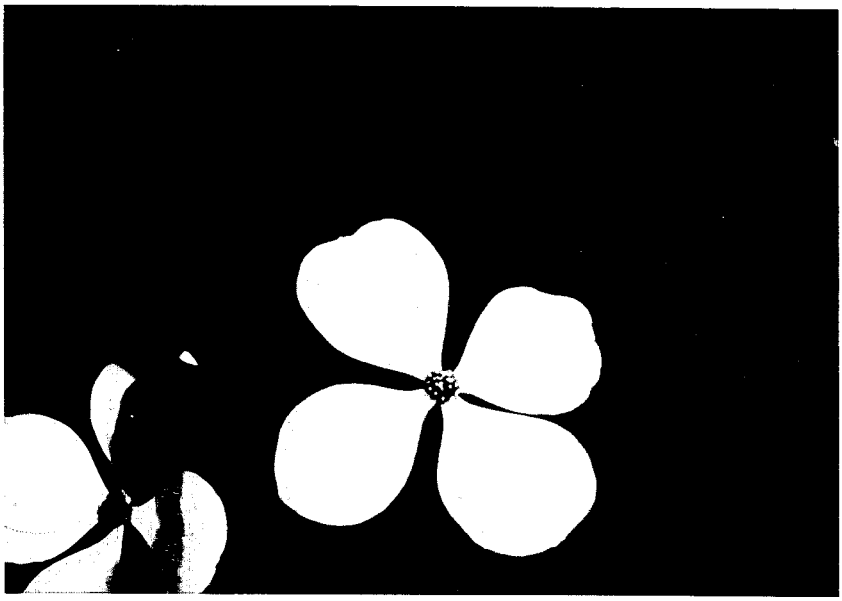
FIG. 1 shows a somewhat enlarged view of floral bracts.
Figure 2:
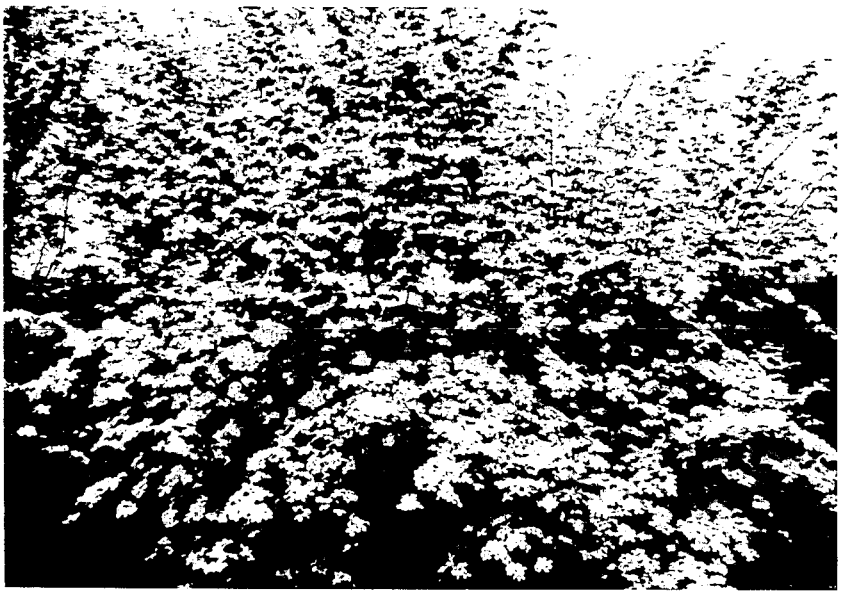
FIG. 2 shows a tree in full bloom so to speak.

Tree: Plant erect as a very young specimen but is vigorous and spreading so it soon develops a form that is densely branched and foliaged close to the ground such that the tree appears full and spreading throughout its entire height; at the end of its 19th growing season, the original seedling had attained a height of 5.5 meters (18 feet) and a uniform spread of 6.7 meters (22 feet). Very floriferous but non-productive as tree is highly sterile; typically a regular bearer but there is some tendency toward alternate bearing, as the floral display is somewhat diminished the year following an unusually heavy floral display.

*Hardy.*—In U.S.D.A. Plant Hardiness Zone 6*a* (−5 degrees to −10 degrees F.).

Trunk: Medium size; but becoming shaggy with age, as then exhibits exfoliating bark.

Branches: Medium; smooth.

Lenticels: Numerous, medium.

Leaves: Abundant.

*Length.*—9.0–14.3 cm (average=11.60).

*Width.*—4.2–6.8 cm (average=5.4) at widest point; i.e., slightly longer and wider than those of the *C. kousa* parent and slightly shorter and narrower than those of the *C. florida* parent.

*Shape.*—Elliptic; acuminate tip; base broadly cuneate, often mildly oblique; margin very mildly undulate;

*Color.*—Dark green: color varies slightly during the growing season; upper surface observed to be 137A or 139A (R.H.S. Color Chart — Green Group); lower surface 138B (Green Group) or 191A (Greyed Green Group).

Petioles:

*Length.*—8–16 mm (average 12.2 mm).

Flower buds: (The true flowers are small and numerous and are borne in flower heads. They are relatively inconspicuous. The floral display is provided by large floral bracts that subtend the flower heads. In common terminology and often in the art, the floral bracts are described as though they were the flowers.) Medium size (larger than those of *C. kousa* but smaller than those of *C. florida*); plump; covered with light brown pubescence. Over winter, the lower pair of vegetative bracts on the peduncle extend to the base of the flower head or slightly higher; the upper pair of bracts loosely enclose the true flowers and extend nearly to the tip of the flower head but do not tightly enclose the true flowers. The four floral bracts do not overlap at all and there is considerable variability (20 to 45% of the true flowers are exposed) from flower head to flower head in the degree to which the true flowers are enclosed by the four floral bracts and the uppermost pair of vegetative bracts. Hence, some of the exposed true flowers may winterkill during an unusually cold winter in U.S.D.A. Plant Hardiness Zone 6*a* (−5 degrees to −10 degrees F.).

Floral bracts:

*Shape.*—Round to slightly obovate with a broadly attenuate base and a mucronate tip; the individual bracts do not overlap.

| | Color: | | |
|---|---|---|---|
| | Start of floral display | Mid-season floral disp. | Peak of flor. disp |
| Upper surface | 157B Green-White | 157C Green-White | 155A White |

-continued

| | Color: | | |
|---|---|---|---|
| | Start of floral display | Mid-season floral disp. | Peak of flor. disp |
| Lower surface | 157C Green-White | 157C Green-White | 155A White |

*Size.*—Intermediate in size to those of typical plants of *C. kouse* and *C. florida.* When the floral bracts are fully expanded, the diameter, or spread, of the inflorescence from tip to tip of the opposing inner bracts is about 113 mm; the diameter of the inflorescence as measured from tip to tip of the opposing outer bracts is about 107 mm. The average length of the inner bracts is approximately 55 mm; the average length of the outer bracts is approximately 52.5 mm. The average width of the inner bracts at their widest point is 39 mm; the average width of the outer bracts at their widest point is 41 mm. Bract length and width may show considerable variation from year to year, but the inner bracts typically are longer and narrower than the outer bracts.

*Peduncle length.*—Each flower head is borne on a peduncle, the average length of which has been found to be approximately 4.2 cm at the time of flowering. Absolute peduncle length varies from year to year, but the peduncle length of this hybrid will typically be found to be intermediate to that of plants of the parental clones.

Flowers: The period of floral display (floral bracts) is basically intermediate to that of plants of the parent species; i.e., occurs in early-to-mid May, commencing two to three days prior to the completion of the floral display of late-flowering specimens of *C. florida* and ceasing several days prior to the start of the floral display of typical plants of *C. kousa.* Anthesis of the tiny, relatively inconspicuous, true flowers generally commences two to four days following the onset of the ornamental display of the large, floral bracts and ceases a few days prior to the end of the period of floral display. Thus, the period of pollen release seldom overlaps that of plants of either parent species. The average number of true flowers per flower head of this new hybrid is approximately 31.

Fruit: Fully developed fruit have not been observed, as plants of this new interspecific hybrid are highly sterile. However, a few flower heads may persist for a month or two and exhibit some parthenocarpic development, or enlargement. However, there is no formation of a syncarp as in *C. kousa,* as the flowers in this new hybrid are distinct and separate in the flower head, or on the receptacle.

Insects: In field plantings with *C. kousa* and *C. florida,* Dogwood Borers have ravaged plants of *C. florida,* but have not infested plants of my new $F_1$ interspecific hybrid.

Diseases: In field plantings with *C. florida* and *C. kousa,* my new $F_1$ interspecific hybrid has made vigorous growth and remained in good health whereas many plants of *C. florida* have died as a result of the "dogwood decline" that has decimated cultivated and wild stands of *C. florida* in the East in recent years.

I claim:

1. A new and distinct cultivar of dogwood tree, substantially as herein shown and described, characterized particularly as to novelty by the unique combination of its exceptionally high vigor and highly floriferous small flowering form, similar to its pollen parent as to its dense, spreading form but becoming much taller with age, intermediate to the two parents as to characteristics of the overwintering flower buds, time of flowering, and size of floral bracts, and exhibiting resistance to dogwood borers and "dogwood decline."

* * * * *